United States Patent [19]

Hill

[11] 4,403,991

[45] Sep. 13, 1983

[54] CLOSURES FOR OPEN ENDED OSTOMY POUCH

[75] Inventor: John A. Hill, New Brunswick, N.J.

[73] Assignee: E. R. Squibb & Sons, Inc., Princeton, N.J.

[21] Appl. No.: 864,895

[22] Filed: Dec. 27, 1977

Related U.S. Application Data

[63] Continuation-in-part of Ser. No. 851,099, Nov. 14, 1977, abandoned.

[51] Int. Cl.³ .............................................. A61F 5/44
[52] U.S. Cl. .................................. 604/337; 604/338; 604/341; 604/344
[58] Field of Search ................... 128/283; 150/6, 7, 3; 24/30.5 R; 604/337, 338, 341, 344

[56] References Cited

U.S. PATENT DOCUMENTS

| | | | |
|---|---|---|---|
| 1,748,529 | 2/1930 | Strayer | 150/7 |
| 2,638,898 | 5/1953 | Perry | 128/283 |
| 2,818,069 | 12/1957 | Fenton | 128/283 |
| 3,009,235 | 11/1961 | Mestral | 28/78 |
| 3,055,368 | 9/1962 | Baxter | 128/283 |
| 3,089,493 | 5/1963 | Aalindo | 128/283 |
| 3,198,228 | 8/1965 | Naito | 150/3 |
| 3,203,551 | 8/1965 | Van Loan, Jr. | 210/136 |
| 3,302,647 | 2/1967 | Marsan | 128/283 |
| 3,339,546 | 9/1967 | Chen | 128/156 |
| 3,340,116 | 9/1967 | Naito | 156/92 |
| 3,351,061 | 11/1967 | Nolan | 128/283 |
| 3,371,696 | 3/1968 | Ausnit | 150/3 |
| 3,380,481 | 4/1968 | Kraus | 128/113 |
| 3,462,332 | 8/1969 | Goto | 156/244 |
| 3,506,517 | 4/1970 | Naito | 156/251 |
| 3,507,282 | 4/1970 | Burding | 128/283 |
| 3,523,534 | 8/1970 | Nolan | 128/283 |
| 3,618,606 | 11/1971 | Brown | 128/283 |
| 3,690,320 | 9/1972 | Riely | 128/283 |
| 3,759,260 | 9/1973 | Nolan et al. | 128/283 |
| 3,825,005 | 7/1974 | Fenton | 128/283 |
| 3,865,109 | 2/1975 | Elmore et al. | 128/283 |
| 3,897,780 | 8/1975 | Trousil | 128/283 |

Primary Examiner—Richard J. Apley
Assistant Examiner—T. J. Wallen
Attorney, Agent, or Firm—Lawrence S. Levinson; Stephen B. Davis

[57] ABSTRACT

An open ended ostomy pouch having a folding bar attached to the bottom of the pouch. The folding bar extends on both sides beyond the width of the pouch at the bottom opening and includes interlocking closure components on opposite ends.

4 Claims, 6 Drawing Figures

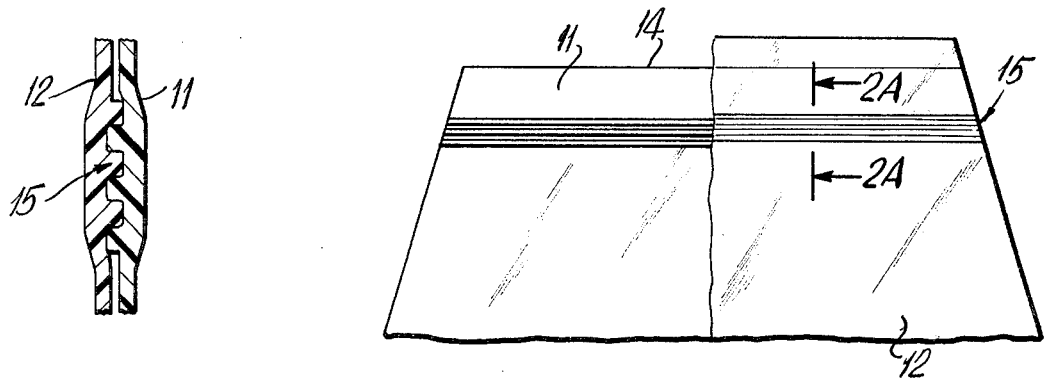
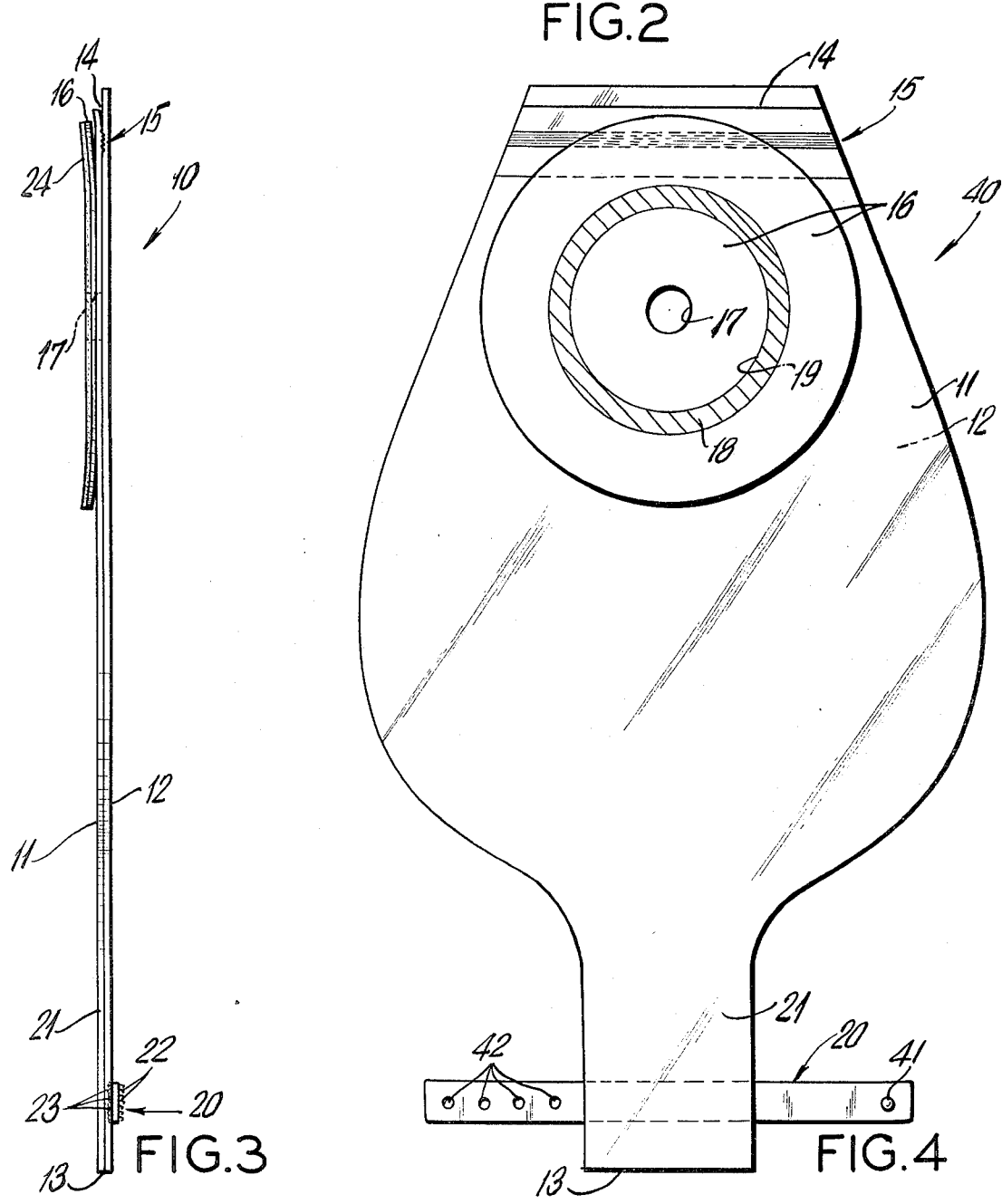

CLOSURES FOR OPEN ENDED OSTOMY POUCH

This application is a continuation-in-part of Ser. No. 851,099 filed on Nov. 14, 1977, now abandoned.

BACKGROUND OF THE INVENTION

Major abdominal surgery for a number of diseases involving different parts of the gastro-intestinal and urinary tract can result in the patient being left with an abdominal stoma. The three most common types of abdominal stoma are the colostomy, the ileostomy, and the ileal conduit. In the case of an ileostomy, the ileal conduit, and many colostomy operations, the patient is unable to control the passage of bodily waste material and must rely upon an appliance attached to their body to collect this material.

Several systems are available for this purpose. The type of system employed varies according to the surgical procedure and the location of the stoma which determine the type and physical consistency of the waste material discharged through the stoma.

Colostomates whose discharge is of a solid consistency usually employ a disposable one or two-piece appliance. The term disposable refers to the fact that the waste collecting pouch portion of the appliance is disposed of after a single use. A closed end pouch sealed along all of its edges with only an opening for the stoma is suitable for this purpose.

Illeostomates and colostomates whose discharge is of a liquid consistency employ systems in which the waste collecting pouch has a bottom opening that permits the contents to be emptied and the pouch reused. Such pouches include some type of a closure means that seals the bottom opening while the pouch is collecting discharge from the stoma.

Several types of closure means have been developed. For example, Nolan in U.S. Pat. No. 3,523,534 discloses an open ended pouch having a closure consisting of a blade like wedge member and a U-shaped trough member. Riely in U.S. Pat. No. 3,690,320 and Burding in U.S. Pat. No. 3,507,282 disclose the use of micro hook and loop elements on the opposite sides of the bottom of the bag that are folded over to seal the bottom of the bag. Fenton in U.S. Pat. No. 3,825,005 discloses an open ended pouch having interlocking ribs and panels on opposite sides of the pouch. Elmore et al. in U.S. Pat. No. 3,865,109 and Brown in U.S. Pat. No. 3,618,606 disclose the use of a clamp to seal the open end of the pouch. Fenton in U.S. Pat. No. 2,818, 069 disclose the use of a snap type closure. Perry in U.S. Pat. No. 2,638,898 disclose the use of a rubber tube that seals the bottom of the pouch against a metal channel.

SUMMARY OF THE INVENTION

This invention is directed to an ostomy appliance having an open ended pouch and an interlocking type closure means located on the folding bar that is bonded to the bottom of the pouch. By attaching the closure directly to the pouch there is no danger that the ostomate will drop the closure while emptying the pouch. Also, by locating the components of the closure means on the outer portions of the folding bar they will not contact the bottom opening of the pouch. As a result, there is less chance that the waste material in the pouch will contact the components of the closure means. Additionally, the closure means is relatively flat and will be unobtrusive under the clothing of the ostomate.

The closure means of this invention can be employed with either a one piece appliance where the pouch includes a mounting gasket or faceplate or a pouch that is attached to the body by a separate double sided adhesive disk. Also, the pouch can include a resealable top opening which permits the ostomate to clean and redress the area contiguous to the stoma without removing the appliance.

BRIEF DESCRIPTION OF THE DRAWINGS

FIG. 2 is an enlarged partial view of the resealable top opening shown in FIG. 1.

FIG. 2A is a sectional view taken along lines 2A—2A of FIG. 2.

FIG. 3 is a side elevation of the ostomy appliance of FIG. 1.

FIG. 4 is a front view of the skin side of an ostomy appliance including an alternate type of bottom closure.

DETAILED DESCRIPTION

This invention is directed to a bottom closure which enables the ostomate to quickly and easily drain the contents of the pouch and then just as quickly and easily reseal the pouch. The closure is permanently attached to the pouch so that it can not be misplaced or dropped during the draining procedure. Also, the components of the closure means are located away from the bottom opening of the pouch so as to prevent their coming into contact with the waste material stored within the pouch.

For convenience this invention will be described as it would be employed with a one-piece semi-permanent ostomy appliance. However, by modifications that will be described below, the closures could also be employed with a two-piece appliance.

Figure 1:
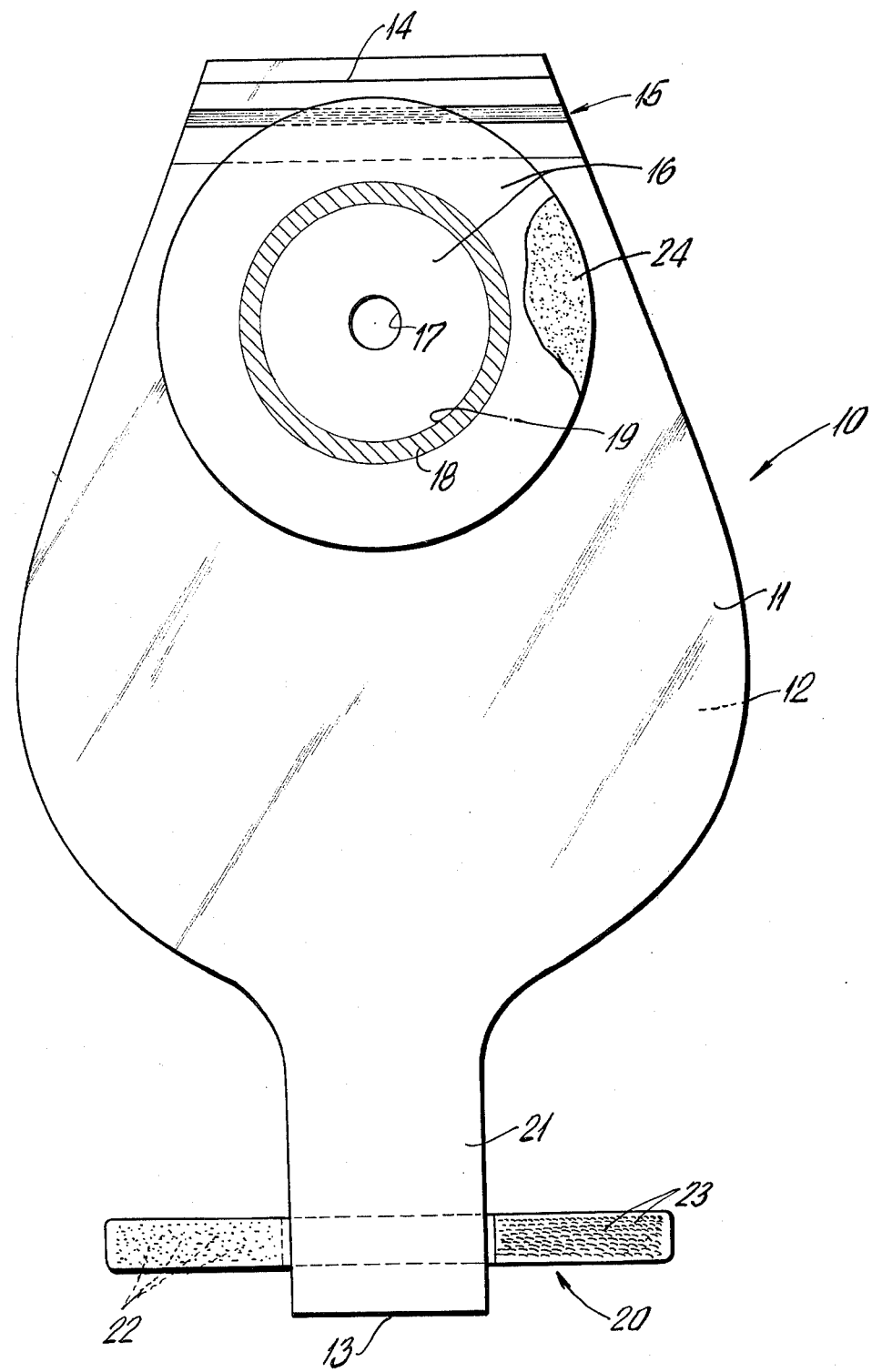
FIG. 1 is a front view of the skin side of an ostomy appliance where the pouch includes a mounting gasket, resealable top opening, and the preferred bottom closure.
Figure 5:
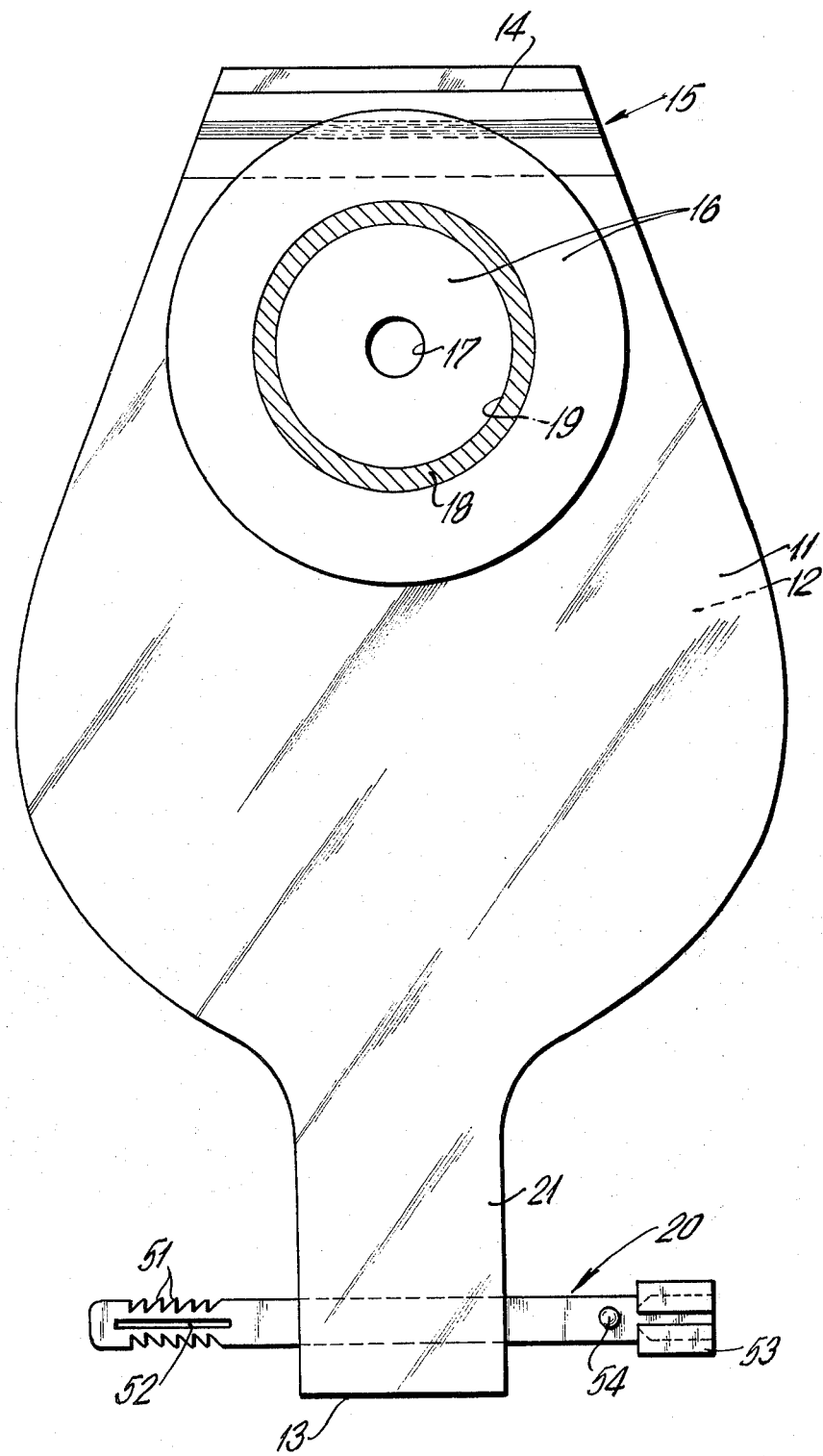
FIG. 5 is a front view of the skin side of an ostomy appliance including another type of bottom closure.

The preferred ostomy appliance of this invention is shown in FIGS. 1 and 3. The appliance 10 includes a pouch formed from polymeric film surfaces 11 and 12 permanently sealed along a majority of their edges by heat or other means known in the art. Sides 11 and 12 are not joined along either the bottom edge 13 or top edge 14. Side 11 is the skin side of the appliance and side 12 is the outer side. There is an opening 19 in sidewall 11 through which the stoma protrudes. The pouch is preferably of a general pear shape with a narrow tail portion 21.

The film surfaces 11 and 12 can be formed from any suitable polymeric material which is moisture proof and odor proof and has the necessary strength. Suitable materials include polyethylene, a copolymer of vinyl chloride and polyvinylidene chloride, etc., and laminates thereof such as a laminate of ethylene vinylacetate or polyethylene and a copolymer of vinyl chloride and polyvinylidene chloride. Both polymeric film surfaces 11 and 12 can be clear or opaque or the skin side 11 can be clear and outside 12 opaque. The thickness of the films 11 and 12 will vary depending upon the particular polymeric material but generally will range from about 2 to about 8 mils.

A mounting gasket or faceplate comprising a flexible film 16 of rubber or polymeric material and a pressure sensitive adhesive layer 24 (note FIG. 3) is permanently bonded by heat, adhesive, or other known means to skin side 11 around opening 19. The area of the bond between the faceplate and side 11 is represented as cross-hatched area 18 in FIG. 1. As can be seen in FIG. 3, the outer peripheral edge of the faceplate is free from side 11 and can thus conform to the body of the ostomate. A starter hole 17 is provided in the faceplate. The ostomate increases the size of the starter hole 17 according to the diameter of the stoma. Of course, the bonding area 18 must remain intact. The adhesive layer 24 is formed from materials known to be compatible with the skin and capable of forming a sufficiently strong bond to support the weight of an ostomy appliance. Suitable adhesive compositions can include a pressure sensitive adhesive component and one or more hydrocolloid materials. Karaya based adhesive compositions such as that taught in U.S. Pat. No 3,302,647 can also be employed. Other suitable adhesive compositions containing guar gum are taught by Chen et al. in U.S. Ser. No. 804,673 filed on June 8, 1977. The preferred adhesive composition is taught by Chen in U.S. Pat. No. 3,339,546 and is a homogeneous blend on a weight percent basis of 40% polyisobutylene, 20% pectin, 20% gelatin, and 20% sodium carboxymethylcellulose. The adhesive layer 24 can vary in thickness at from about 50 to about 150 mils. The faceplate is normally disk shaped as shown in FIG. 1 but can be formed in other shapes such as rectangular if desired. Optionally, a ring shaped pressure plate (not shown in the drawings) having a belt attachment can be fitted between the faceplate and surface 11. Also, during shipping the exposed surface of the adhesive layer 24 is covered by a piece of silicone coated release paper.

Preferably, the polymeric film surfaces 11 and 12 are formed from a laminate composed of an outer and inner layer of ethylene vinyl acetate having as core material a layer of a copolymer of vinyl chloride and polyvinylidene chloride and film surfaces 11 and 12 are each about 3 mils thick. Also, preferably skin side film surface 11 is clear and outer film surface 12 is opaque. Preferably, flexible film 16 is formed from polyethylene of about 2 mils thickness.

A folding bar 20 of semi-rigid polymeric material is permanently bonded to the pouch near the bottom of tail area 21. Folding bar 20 extends beyond the width of tail area 21 on both sides. The bar 20 is preferably formed of high density polyethylene of from about 5 to about 10 mils or low density polyethylene of from about 10 to about 25 mils. The folding bar 20 as shown in FIGS. 1, 3, 4 and 5 is preferably bonded to the outer pouch side 12 but could alternatively be bonded to the skin side 11. The folding bar 20 is attached to the pouch by adhesive, heat sealing if the polymeric materials of the pouch and folding bar are compatible, or by the combination of adhesive and heat sealing.

The preferred closure shown in FIGS. 1 and 3 comprises a section of hook type male elements 23 attached to one end of folding bar 20 and female type loop elements 22 attached to the other end of folding bar 20. The folding bar 20 is preferably formed of high density polyethylene of about 5 mils thickness and is attached to the outer pouch side 12 by means of both adhesive and heat sealing. The male elements 23 face toward the body and the female loop elements 22 face outward away from the body. The method of forming such male and female elements is taught by de Mestral in U.S. Pat. No. 3,009,235.

The seal is formed by rolling the tail area 21 of the pouch up over the folding bar 20 on the skin side for three folds so that the male hook elements 23 and female loop elements 22 can be pressed together on the outer side of the pouch. Of course, the tail area 21 could be rolled up on the outside of the pouch and the folding bar 20 bent so that elements 23 and 22 are pressed together on the skin side of the pouch.

The appliance 10 also includes a resealable opening 15 across the top of the pouch above the stomal opening. By means of this opening the ostomate is able to examine and clean the area of skin contiguous with the stoma and, if necessary, redress this area with an ostomy powder or ointment without the necessity of first removing the appliance. By so treating, the rate of erosion of the adhesive and the skin barrier are reduced and the appliance can remain in place for a longer period of time.

The resealable opening means 15 near the stomal opening is shown in FIGS. 1 and 3 and in greater detail in FIGS. 2 and 2A. As shown in FIGS. 2 and 2A, alternate rows of raised ridges separated by grooves are present on the inside of polymeric surfaces 11 and 12. The rows are aligned so that the raised ridges on the inside of film 12 can be forced by the exertion of a slight amount of pressure into a groove on the inside of surface 11. The seal formed is fluid and odor tight. Methods of forming this and other equivalent types of interlocking surfaces on polymeric films are taught in various references such as by Kraus in U.S. Pat. No. 3,380,481, Ausnit in U.S. Pat. No. 3,371,696, by Naito et al. in U.S. Pat. Nos. 3,198,228 and 3,246,672 and by Goto in U.S. Pat. No. 3,462,332. As shown in FIGS. 2 and 3 the upper edge of film surface 12 extends beyond the upper edge of film surface 11 so as to aid in pulling the two surfaces apart.

The appliance 40 shown in FIG. 4 is identical to appliance 10 except for the closure means located near the bottom opening 13. The adhesive layer 24 has not been included in the figure. The closure again consists of a folding bar 20 of semi-rigid polymeric material that is permanently bonded to pouch near the bottom of tail area 21. Again, the folding bar is preferably formed of high density polyethylene of from about 5 to about 10 mils or low density polyethylene of from about 10 to about 25 mils thickness and is bonded by means of adhesive, heat sealing, or a combination of both, to the outer pouch side 12. The closure means consists of a series of holes 42 located on one side of folding bar 20 and a knob like element 41 also of semi-rigid polymeric material located on the other extended portion of the folding bar. The knob like element 41 projects toward the skin side of the appliance and is dimensioned so that it can be pushed through one of the holes 42 by the erection of a slight amount of force. The seal is again formed by rolling the tail area 21 of the pouch up over the folding bar 20 on the skin side for three folds and then bending the ends of the folding bar 20 so that the appropriate hole 42 can be pushed down over knob 41. Preferably, the folding bar 20 including knob-like element 41 is formed as a single unit such as by molding. Of course, the folding bar 20 could be attached to the skin side 11 of the pouch and the seal could be formed by rolling the tail area 21 up on the outer side of the pouch.

The appliance 50 shown in FIG. 5 is again identical to appliance 10 except for the closure means located near the bottom opening 13. The adhesive layer 24 has not been included in this figure. The closure again includes semi-rigid polymeric folding bar 20 having the characteristics described above. In this embodiment, one extended end of folding bar 20 has a centrally located groove like opening 52 and serrated edges 51 and the other extended portion of bar 20 includes a protruding button like element 54 and on the end of bar 20 a relatively rigid element 53 that partially encircles the bar 20 so as to form a channel or keyway as represented by the broken lines. The seal is formed by again rolling tail area 21 of the pouch up over the folding bar on the skin side for three folds and then bending the ends of the folding bar so that button like element 54 can be forced into groove 52. The semi-rigid end of folding bar 20 can then be pulled through the channel in rigid element 53 so that the serrated edges will lock into a tight fit. The seal is opened by forcing element 54 out of groove 52 and then twisting the semi-rigid end of the folding bar so that the serrated edges are no longer locked into the channel. This folding bar including the button like element 54 and element 53 is preferably formed as a single unit such as by molding.

Appliances 10, 40, and 50 are employed in the same manner. The ostomate enlarges the starting hole according to the size of his stoma. The bottom closure is sealed as explained above. The silicone coated release paper is removed from adhesive layer 24 and the area of skin around the stoma is cleaned, dried and dressed. With the top closure open the appliance is fitted with the top opening enabling the ostomate to perform the fit with greater ease. The top closure is then sealed. At any time while the appliance is in place the ostomate is able to open the top seal and examine the stomal area. If necessary, the area can be cleaned by use of a cotton swab passed down through the opening and the area can also be redressed with ointment or other medication. The opening is then resealed. Of course, at periodic intervals the bottom seal is opened to drain the contents of the pouch. If desired, the interior of the pouch may be flushed through the top opening for cleaning purposes. Also, gas within the pouch can be expelled by opening and closing the top of the pouch.

This invention has been described with reference to a semi-permanent one-piece appliance. However, it is also applicable to other ostomy appliances. For example, the adhesive layer 24 can be omitted so that the faceplate is merely a film of polymeric material and a separate double sided pressure sensitive adhesive disk is employed to mount the appliance. Also, the pouch can include a deodorizing and/or vent means as disclosed, for example, by Riely in U.S. Pat. No. 3,690,320, by Nolan et al. in U.S. Pat. No. 3,759,260 and by Elmore et al. in U.S. Pat. No. 3,865,109.

What is claimed is:

1. An ostomy appliance comprising a generally pear shaped pouch formed from two polymeric film surfaces permanently bonded along a majority of their length, each of said pouch polymeric film surfaces being a laminate of about 3 mils thickness of an outer and inner layer of ethylene vinyl acetate having a core of a copolymer of vinyl chloride and polyvinylidene chloride, one of said polymeric film surfaces being the skin side of said pouch and having an opening which fits around the stoma, the other polymeric film surface being the outer side of said pouch, a faceplate permanently bonded to the skin side of the pouch around said stomal opening, said faceplate having a centrally located opening which is expanded to fit the appliance snugly around the stoma and comprises a thin disk shaped film of polymeric material of from about 2 to 8 mils thickness having an adhesive composition which includes a pressure sensitive adhesive component and one or more hydrocolloids on its exposed surface and wherein the bond between said disk shaped film and said skin side of the pouch does not extend to the outer peripheral edge of said faceplate, said pouch including a narrow tail portion having an open bottom through which the contents of said pouch can be drained, and resealable bottom closure means comprising a semi-rigid folding bar of high density polyethylene of about 5 mils thickness permanently attached to the outer side of said pouch at the narrow tail portion near said bottom opening, said folding bar extending traversely across and beyond the width of said pouch tail portion and having interlocking closure elements on said extended portions of said folding bar wherein said interlocking closure elements are a section of male hook elements attached to the skin side of one extending portion of said folding bar and a section of female loop elements attached to the outer side of the other extended portion of said folding bar and wherein said bottom opening is sealed by rolling the tail portion of said pouch over said folding bar and bending the extended portions of said folding bar so that said male hook and female loop elements can be pressed together.

2. The appliance of claim 1 wherein said faceplate comprises a polyethylene film of about 2 mils thickness having as the adhesive composition from about 50 to about 150 mils of a homogeneous mixture on a weight percent basis of about 40% polyisobutylene, about 20% pectin, about 20% gelatin, and about 20% sodium carboxymethylcellulose.

3. The appliance of claim 2 wherein said skin side polymeric film surface is clear and said outer side polymeric film surface is opaque and said appliance includes a resealable opening across the top of said pouch above the stomal opening said top opening comprising interlocking surfaces on the inside of each of said polymeric film surfaces.

4. The appliance of claim 3 wherein said interlocking surfaces are a series of alternating raised ridges and grooves extending across the top of said pouch which are aligned so that by the exertion of a slight amount of pressure the raised ridge on the inside of one surface will fit within the groove on the inside of the other surface.

* * * * *